United States Patent [19]

Wolrich

[11] Patent Number: 5,423,782

[45] Date of Patent: Jun. 13, 1995

[54] DISPOSABLE OSTOMY BAG LINER

[76] Inventor: Douglas H. Wolrich, 1360 Chesterfield Ave., North Vancouver, British Columbia, Canada, V7M 2M9

[21] Appl. No.: 262,160

[22] Filed: Jun. 17, 1994

[51] Int. Cl.⁶ .............................. A61F 5/44
[52] U.S. Cl. .................................. 604/339
[58] Field of Search ............... 604/333, 334, 338, 339

[56] References Cited

U.S. PATENT DOCUMENTS

| | | | |
|---|---|---|---|
| D. 323,029 | 1/1992 | Doss | D24/121 |
| 3,089,493 | 5/1963 | Galindo . | |
| 3,902,496 | 9/1975 | Eakin | 604/334 |
| 4,439,191 | 3/1984 | Hogan | 604/332 |
| 4,816,027 | 3/1989 | Gilchrist et al. | 604/339 |
| 4,826,495 | 5/1989 | Petersen | 604/333 |
| 4,930,942 | 6/1990 | Keyes et al. | 406/49 |
| 4,940,461 | 7/1990 | Steer | 604/333 |
| 5,209,744 | 5/1993 | Abe et al. | 604/342 |
| 5,250,042 | 10/1993 | Torgalkar et al. | 604/333 |
| 5,306,264 | 4/1994 | Ferguson et al. | 604/333 |

Primary Examiner—Jerome L. Kruter
Attorney, Agent, or Firm—Bull, Housser & Tupper

[57] ABSTRACT

A disposable ostomy bag liner apparatus including a unitary flexible bag having a main body portion, a tapered portion, a narrowed portion and a flange portion. The tapered portion is disposed adjacent the main body portion and together, the main body portion and tapered portion define an interior portion of the bag for receiving and hold intestinal waste material. The narrowed portion is disposed adjacent the tapered portion and is for holding the bag in place during insertion of the bag in an opening of a bag flange of a conventional ostomy bag. The narrowed portion defines a mouth opening in the bag for admitting intestinal waste material into the interior portion. The flange portion is adjacent the narrowed portion, and cooperates with the bag flange to secure and seal the liner to an ostomy flange on the patient. A guard is disposed in the flexible bag to define a guarded region in the bag and guards the waste material received in the mouth opening from the guarded region to generally inhibit access of the waste material to the guarded region to prevent movement of the waste material into the guarded region.

16 Claims, 4 Drawing Sheets

DISPOSABLE OSTOMY BAG LINER

BACKGROUND OF THE INVENTION

This invention relates to ostomy bags and more particularly to a disposable ostomy bag liner for use with a conventional ostomy bag.

Conventional ostomy bags for colostomy and some ileostomy patients are frequently changed at least once per day. The cost of such bags is significant, especially where the patient must bear the entire cost of a supply of ostomy bags.

To reduce the number of conventional ostomy bags required for colostomy and some ileostomy patients, various schemes have been suggested to provide ostomy bag liners, allowing such liners to be discarded at least once per day and allowing the conventional ostomy bag to be used for perhaps one week or more. If the cost of such liners is relatively inexpensive compared to the cost of the conventional ostomy bags, the patient can enjoy a significant cost saving.

U.S. Pat. No. 3,089,493 to Galindo discloses a colostomy bag with disposable liner which requires the use of a separate plastic flange which must be pulled into the liner so as to provide a liquid-proof connection about an opening in the bag liner with an opening in the colostomy bag. It will be appreciated that often ostomy patients are aged and do not have the dexterity required to manipulate such a flange, making the use of this device frustrating.

U.S. Pat. No. 4,816,027 Gilchrist et al. discloses a disposable ostomy bag liner which has an affixed apertured collar designed to extend over a collar peripheral surface of a fastening element. There appears to be no disclosure of means for venting gas from the liner and therefore it is possible the liner could expand as gas is admitted into the liner.

The deficiencies in the devices described in the above two patents indicate that there is a need for an ostomy bag liner for use by colostomy and some ileostomy patients which is easy to install in a conventional ostomy bag, which has provisions to allow for the escape of gas admitted into the liner and which is relatively inexpensive to produce. The present invention addresses the above needs.

SUMMARY OF THE INVENTION

In accordance with one aspect of the invention, there is provided a disposable ostomy bag liner apparatus including a unitary flexible bag having a main body portion, a tapered portion, a narrowed portion and a flange portion. The tapered portion is disposed adjacent the main body portion and together, the main body portion and tapered portion define an interior portion of the bag for receiving and hold intestinal waste material. The narrowed portion is disposed adjacent the tapered portion and is for holding the bag in place during insertion of the bag in an opening of a bag flange of a conventional ostomy bag. The narrowed portion defines a mouth opening in the bag for admitting intestinal waste material into the interior portion. The flange portion is adjacent the narrowed portion, and cooperates with the bag flange to secure and seal the liner to an ostomy flange on the patient. A guard is disposed in the flexible bag to define a guarded region in the bag and guards the waste material received in the mouth opening from the guarded region to generally inhibit access of the waste material to the guarded region to prevent movement of the waste material into the guarded region.

Preferably, the flexible bag is formed from first and second flexible sheet portions, the first and second flexible sheet portions having joined and unjoined perimeter edge portions, the joined perimeter edge portions generally defining the main body portion, the tapered portion and the narrowed portion, and at least two of the joined perimeter edge portions and the joined perimeter edge portions generally defining the flange portion.

Preferably, the flange portion has an inverse taper and extends generally radially about and beyond the mouth opening by at least approximately 0.5 inches.

Preferably, the tapered portion tapers toward the narrowed portion.

Preferably, the body portion is defined by first and second joined opposite side edge portions and a bottom joined edge portion extending between the first and second opposite joined edge portions and preferably, the tapered portion is defined by first and second tapered joined edges extending from and at respective angles to the first and second joined opposite side edges and preferably, the flange portion is at least partially defined by first and second angled, joined flange edges extending from and at respective angles to the first and second joined tapered edges respectively.

Preferably, the joined edges are laminated together to join corresponding edges on the first and second sheets together.

Preferably, the flexible bag is formed from a disposable material including a transparent, low density polyethylene plastic having a thickness of between 0.001 and 0.002 inches.

Preferably, the apparatus includes at least one gas vent opening disposed in the guarded region of the flexible bag prior to installation in the conventional ostomy bag. The at least one gas vent opening may include first and second pairs of gas vent openings, each gas vent opening having a diameter of between approximately 0.025 inches and being disposed in the guarded region.

Preferably, the guarded region is disposed in the tapered portion and preferably, the guard includes a laminated joint line joining the first and second sheet portions together along a line disposed between the gas vent opening and the interior portion of the bag and extending generally from a joined perimeter edge portion into the interior portion of the bag.

According to another aspect of the invention there is provided a disposable ostomy bag liner apparatus for use in a conventional ostomy bag having an air vent opening, the ostomy bag liner including a flexible bag having a mouth opening for receiving intestinal waste material from an intestine and having an interior portion for storing the intestinal waste material, at least one gas vent opening for venting gas into the conventional ostomy bag and a guard disposed in the interior portion for guarding the waste material, received in the mouth opening, from the at least one gas vent opening to generally inhibit the access of the waste material to the at least one gas vent opening to prevent the waste material from exiting the at least one gas vent opening.

Preferably, the flexible bag includes a flange portion extending about the mouth opening for cooperating with an ostomy flange to secure and seal the liner to the ostomy flange.

Preferably, the flexible bag is formed from a membrane having a thickness of between 0.001 and 0.002 inches, the flange portion having a thickness no greater than the thickness of the membrane, to permit the flange portion to be received between cooperating flanges of a conventional ostomy flange and a conventional ostomy bag flange.

In accordance with another aspect of the invention, there is provided a method of receiving intestinal waste material in a disposable ostomy bag liner, the method comprising the steps of:

a) receiving intestinal waste material, in a mouth opening of an ostomy bag liner disposed in an ostomy bag; and b) guarding the waste material, received in the mouth opening, from at least one gas vent opening in the liner to generally inhibit the access of the waste material to the at least one gas vent opening to prevent the waste material from exiting the at least one gas vent openings.

In accordance with another aspect of the invention, there is provided a disposable ostomy bag liner including:

a) a unitary flexible bag formed from first and second flexible sheet respectively, the first and second flexible sheet portions having laminated and unlaminated perimeter edge portions, the laminated perimeter edge portions generally defining;

i) a main body portion;

ii) a tapered portion adjacent the main body portion, the main body portion and tapered portion defining an interior portion of the bag for receiving and hold intestinal waste material;

iii) a narrowed portion adjacent the tapered portion, for holding the bag in place during insertion of the bag in an opening of a bag flange on a conventional ostomy bag, the narrowed portion defining a mouth opening in the bag for admitting the intestinal waste material into the interior portion; and iv) a flange portion adjacent the narrowed portion, for cooperating with an ostomy flange to secure and seal the liner to the ostomy flange, the flange portion being defined by at least two of the joined perimeter edge portions and the joined perimeter edge portions; and b) first and second pairs of gas vent openings disposed generally adjacent respective laminated edge portions generally on opposite sides of the bag; and c) first and second laminated joints joining the first and second flexible sheet portions, together along first and second lines respectively, the first and second lines being disposed between the first and second pairs of gas vent openings and the interior portion of the bag respectively and extending from respective laminated edge portions adjacent the first and second pairs of openings respectively, the first and second laminated joints acting to guard the waste material received in the mouth opening from the first and second pairs of gas vent openings respectively to generally inhibit the access of the waste material to the first and second gas vent openings respectively to prevent the waste material from exiting said at least on gas vent opening.

By making the liner out of the polyethylene and by laminating together the edge portions of the bag, the bag is quickly and easily formed from sheet polyethylene. In addition, the formation of the guards in the liner to define the guarded areas is simply and easily achieved by further laminations, which can be done at the time the edge portions are laminated. Hence the cost of producing a liner according to the invention is relatively inexpensive.

The guard areas provide pre-defined areas in which a user can form gas vent openings. Alternatively, the gas vent openings can be formed at the time of manufacture. The guards prevent intestinal waste material from entering the guarded regions in which the gas vent openings are ultimately formed and thereby prevent intestinal waste material from exiting the liner through the gas vent openings, but do allow gas to escape.

The flange portion formed in the first and second sheets is easily separable and spreadable about the ostomy bag opening by a person of even minimal dexterity as this action requires no tugging or pulling to stretch resilient rings or the like about the opening. Furthermore, the flange portion is less dependent on manufacturing tolerances because to properly seal the flange portion when the ostomy bag is connected to flange coupling on the patient, it is necessary only to ensure that the entire bag coupling is covered by the flange portion.

BRIEF DESCRIPTION OF THE DRAWINGS

In drawings which illustrate embodiments of the invention.

DETAILED DESCRIPTION

Conventional Ostomy Bag and Ostomy Flange

Figure 1:
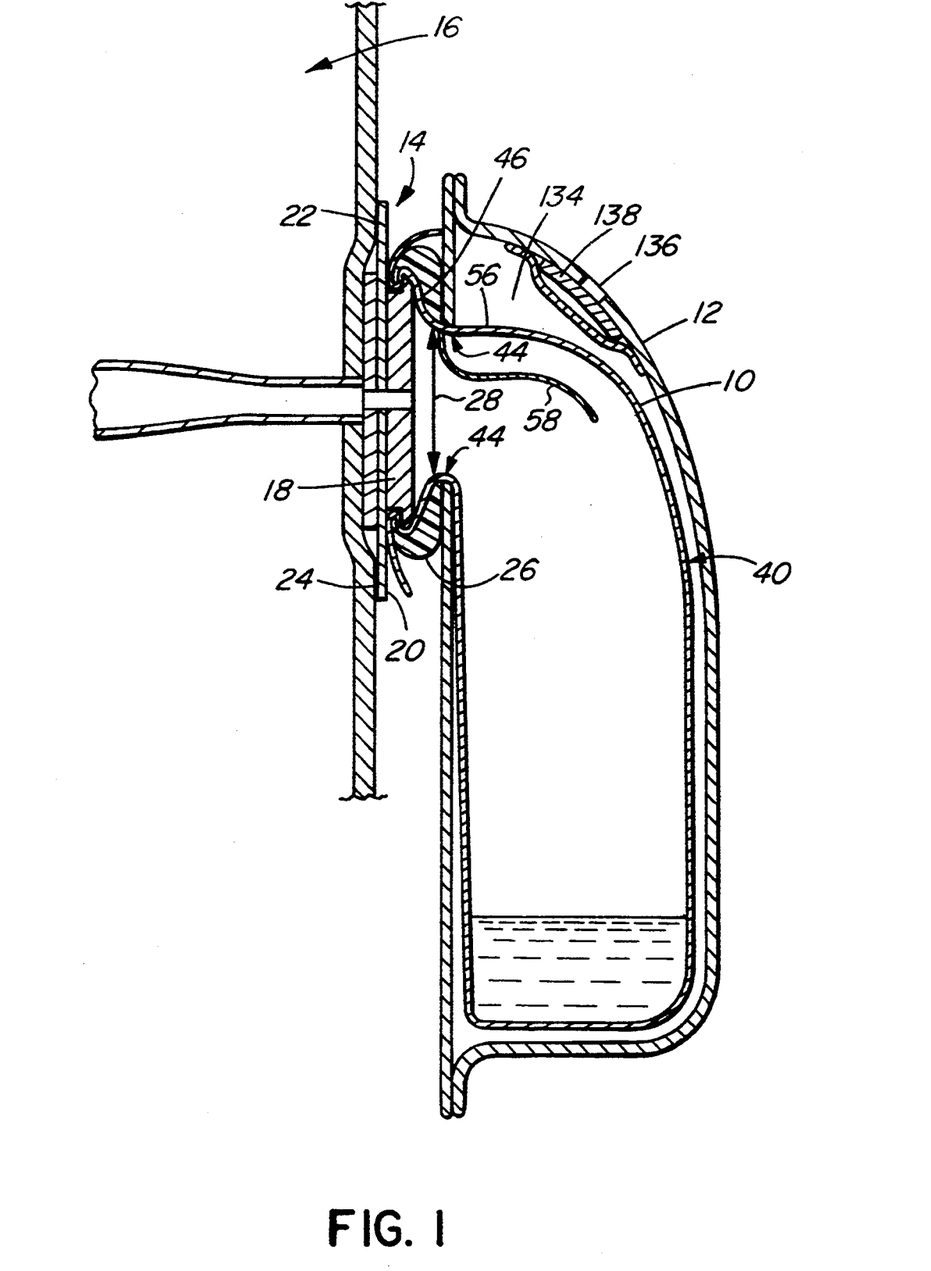
FIG. 1 is a cross sectional view of a disposable ostomy bag liner according to a first embodiment of the invention, shown installed in a conventional ostomy bag.

Referring to FIG. 1, a disposable ostomy bag liner according to a first embodiment of the invention is shown generally at 10 installed in a conventional ostomy bag 12 secured to a conventional ostomy flange 14 fitted to an ostomy patient 16. The ostomy flange 14 includes a circular plastic flange coupling 18 to which is secured an annular flexible securing member 20 having adhesive areas 22 and 24 for securing the ostomy flange 14 to the patient 16. The ostomy bag 12 has a complementary bag coupling 26 which connects to the flange coupling 18 to connect the ostomy bag 12 to the ostomy flange 14 in generally fluid-tight relation. The bag coupling 26 has an opening 28 through which intestinal waste material is conventionally admitted into the conventional ostomy bag. In this embodiment however, only the liner 10 is inserted into the opening 28 and the intestinal waste which otherwise would have been admitted into the conventional ostomy bag 12 is admitted only into the disposable ostomy bag liner 10 according to the invention.

Connection of Conventional Ostomy Bag to Ostomy Flange

Figure 2:
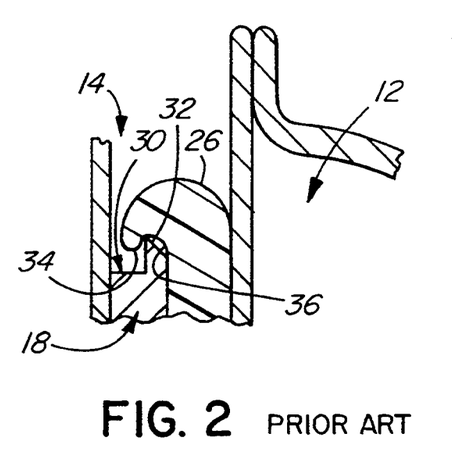
FIG. 2 is a cross sectional view of a conventional flange coupling and conventional ostomy bag coupling according to the prior art.

Referring to FIG. 2, the connection of the conventional ostomy bag 12 to the conventional ostomy flange 14 is facilitated by external neck and head portions 30 and 32 respectively on the flange coupling 18 and complementary shaped ring and groove portions 34 and 36 respectively on the bag coupling 26. When the bag 12 is secured to the ostomy flange 14, the ring 34 is retained by the head portion 32 to secure the bag 12 to the ostomy flange 14. The disposable ostomy bag liner according to the invention is intended for use with this type of flange and bag coupling. A bag and coupling of the type described above are available as component numbers SUR-FIT 1784-58 (ostomy bag) and SUR-FIT 225-21 (ostomy flange) from Convatec, a Bristol-Myers Squibb Company, USA EUA PO Box 4000, Princeton, N.J. 08543-4000.

Liner

Figure 3:
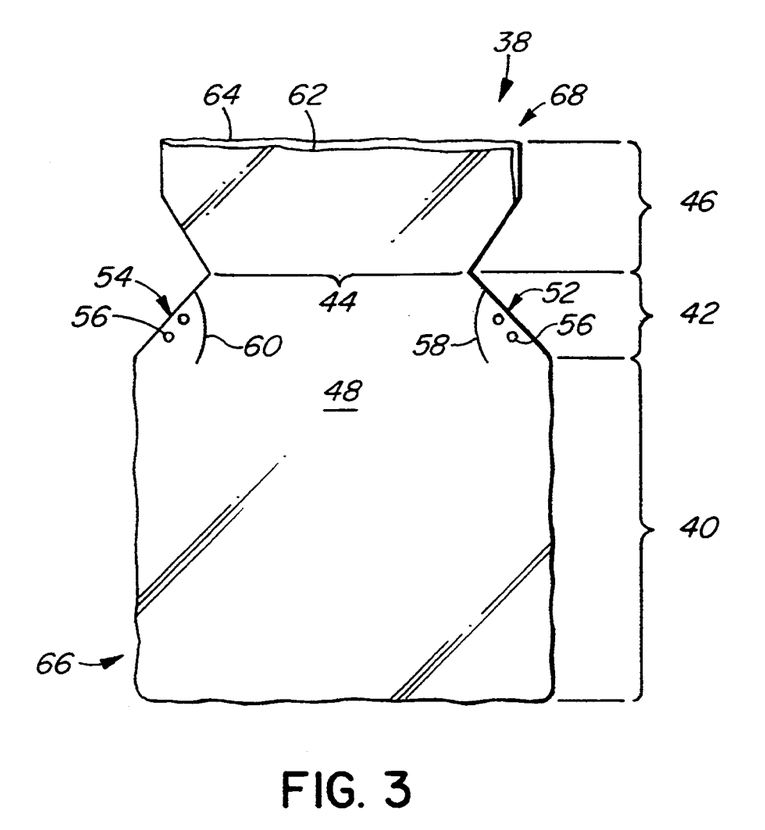
FIG. 3 is a side elevational view of the disposable ostomy bag liner according to the first embodiment of the invention.

Referring to FIG. 3, the liner includes a unitary flexible liner bag 38 having a main body portion 40, a tapered portion 42, a narrowed portion 44 and a flange portion 46. The main body portion 40 and the tapered portion 42 define an interior portion 48 of the bag for receiving and holding intestinal waste material. Referring back to FIG. 1, in use, the main body portion 40 is fully received inside the conventional ostomy bag 12 while only the flange portion 46 extends outside of the conventional ostomy bag. The narrowed portion 44 is disposed between the tapered portion 42 and the flange portion 46 and is for holding the liner bag 38 in place in the opening 28 of the bag coupling 26. Referring back to FIG. 3, the flange portion 46 is disposed adjacent the narrowed portion 44 and is for cooperating with the conventional ostomy flange 14 shown in FIG. 1 to secure and seal the liner bag 38 to the ostomy flange 14. Referring back to FIG. 3, effectively, the narrowed portion defines a mouth opening 50 for admitting intestinal waste material into the interior portion 48 of the liner bag 38.

Still referring to FIG. 3, in this embodiment, the liner bag 38 has first and second pairs 52 and 54 of gas vent openings 56 and has first and second guards 58 and 60 disposed in the flexible bag for guarding the waste material received in the mouth opening from the pairs 52 and 54 of gas vent openings to generally inhibit the access of the waste material thereto to prevent clogging by the waste material.

Liner Construction

Still referring to FIG. 3, the liner bag 38 is formed from first and second flexible sheet portions 62 and 64, together having joined perimeter edges shown generally at 66 and unjoined perimeter edges shown generally at 68.

Figure 4:
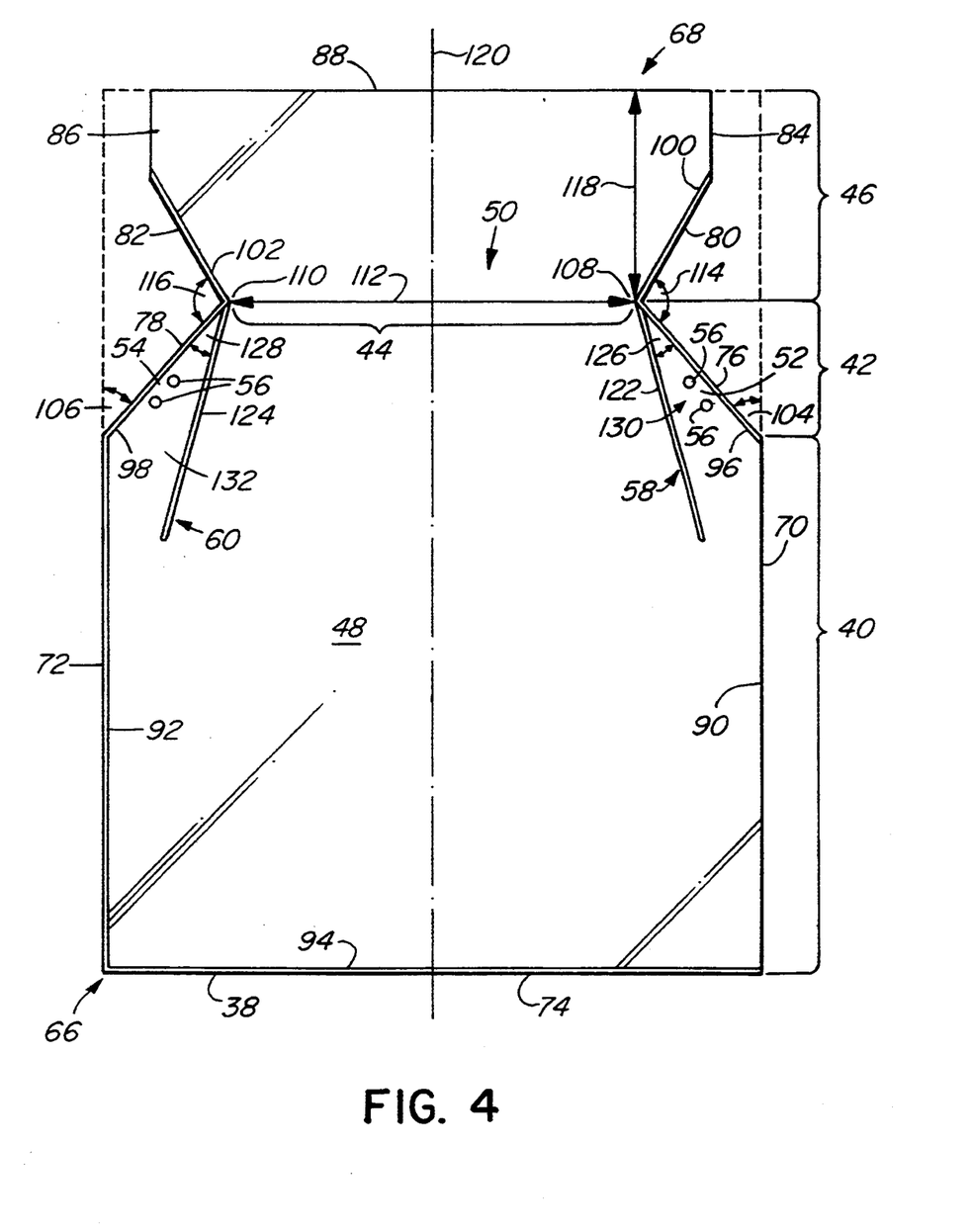
FIG. 4 is a detailed side elevational view of the disposable ostomy bag liner shown in FIG. 3.

Referring to FIG. 4, the joined perimeter edges include generally parallel first and second joined opposite side edge portions 70 and 72 and a bottom joined edge portion 74 extending between the first and second opposite edge portions. The first and second opposite edge portions and the bottom edge portion define the main body portion 40. The joined perimeter edges 66 further include first and second tapered edges 76 and 78 which define the tapered portion 42.

The joined perimeter edges 66 further include first and second flange edges 80 and 82 which partly define the flange portion 46. The remainder of the flange portion 46 is defined by first and second straight edges 84 and 86 and a top edge 88, each of which is unjoined and therefore included in the grouping of unjoined edges defined by reference numeral 68.

Body Portion

Still referring to FIG. 4, the first and second sheet portions and (only the first sheet portion 62 being shown in FIG. 4) may be of a common sheet of 1.0 mil transparent low density polyethylene sheet which is a suitably disposable material capable of being flushed down a conventional toilet. Generally polyethylene sheet material of between 1.0 mil and 2.0 mil (0.001 inches and 0.002 inches) thickness may be used however it will be appreciated that the smaller thicknesses are more susceptible to puncture while the larger thicknesses tend to interfere with the sealing between the bag coupling 26 and the flange coupling 18.

The polyethylene sheet may initially be rectangular in shape and then folded as depicted in broken outline to form the first joined side edge portion 70. Thus, corresponding first side edge portions of the first and second sheet portions are joined together by a fold 90. In this embodiment, each of the remaining joined edges 72, 74, 76, 78, 80, 82, and is joined together by a respective heat lamination 92, 94, 96, 98, 100, 102. Such lamination can be achieved by overlapping the first and second sheet portions and rolling thereon a heated roller (not shown), heated sufficiently to fuse the first and second sheet portions together on contact with the roller.

In this embodiment, the heat laminations 92-102 are formed in overlapping rectangular sheet portions such that the indicated corresponding edges on the first and second sheets are joined together. Then, each of the edges, with the exception of the first joined side edge portion 70 is cut out of the resulting laminated bag, in the shape as shown in solid outline.

Tapered Portion

Still referring to FIG. 4, the first and second tapered edges 76 and 78 extend at respective similar angles 104 and 106 to the first and second joined opposite side edges respectively such that the tapered edges taper inwardly of the first and second side edge portions 70 and 72 such that the tapered portion 42 tapers toward the narrowed portion 44. In this embodiment, the angles 104 and 106 are each approximately 45 degrees.

Narrowed Portion

The first and second tapered edges 76 and 78 are terminated at respective points 108 and 110 which are spaced apart by a distance 112 to define the narrowed portion. This distance is determined by the diameter opening in the ostomy flange. Generally, this distance is given by the function:

$$d = (pi)D/2$$

where d is the distance (112); and D is the diameter of the opening in the ostomy flange Flange Portion The flange portion 46 is at least partially defined by the first and second angled, joined flange edges 80 and 82 extending from and at respective angles 14 and 116 to the first and second joined tapered edges 76 and 78 respectively. The angles 114 and 116 between the first and second joined tapered edges 76 and 78 and the first and second joined flange edges 80 and 82 should be in the range of between 60 and 120 degrees, but preferably are approximately 90 degrees. Generally, the greater the angle, the greater the tendency of the liner bag 38 to be held in the conventional ostomy bag but, the greater the susceptibility to tearing of the liner bag 38. The angular orientation of the flange edges 80 and 82 provides the flange portion 46 with an inverse taper, or in other words, the flange edges diverge from the narrowed portion 44. Since the narrowed portion 44 defines the mouth opening 50, the flange portion 46 extends about the mouth opening 50. Preferably, the flange portion 46 extends a distance 118 of at least 0.5 inches radially beyond the mouth opening 50 to provide enough material in the flange portion 46 to permit the flange portion to be located between the flange coupling and the bag coupling shown in FIG. 2.

Referring back to FIG. 4, the first and second straight edges 84 and 86 extend generally parallel to a longitudinal axis 120 of the liner bag 38 and are unjoined to permit the patient easy access to upper portions of the first and second sheet portions 62 (and 64, not shown in FIG. 4). In addition, the top edge 88 of the bag is unjoined to provide access to the mouth opening 50 of the bag. The unjoined straight edges 84, 86 and top edge 88 allow the patient to spread apart the flange portions 46 of each sheet portion to permit the flange portions to be spread about the bag coupling during installation of the liner bag 38 into the conventional ostomy bag.

Guards

In addition to laminating together certain edges of the sheet portions as described above, first and second heat laminated joint lines 122 and 124, extending from the first and second tapered edges 76 and 78 respectively, are formed in the tapered portion 42. The first and second heat laminated joint lines 122 and 124 generally extend at first and second acute angles 126 and 128 relative to the first and second tapered edges 76 and 78 to define first and second guarded regions 130 and 132 in the tapered portion 42, which are separated from the interior portion 48 of the bag. The first and second pairs 52 and 54 of gas vent openings are formed in the tapered portion 42, in the first and second guarded regions 130 and 132 respectively, and the first and second heat laminated joint lines 122 and 124 act as the first and second guards 58 and 60 for guarding the waste material received in the mouth opening 50 from the pairs 52 and 54 of gas vent openings.

The first and second pairs 52 and 54 of gas vent openings 56 are formed in the first and second guarded regions 130 and 132 simply by puncturing these areas with a conventional No. 10 pin (not shown) having a diameter of approximately 0.025 inches. Preferably, the gas vent openings each have a diameter of between 0.020 and 0.030 inches. During manufacture of the liner bag 38, the gas vent openings 56 may omitted therefrom and the patient may be invited to form these openings as required, to suit the patient's individual level of gas production. However the gas vent openings 56 are formed, at least one gas vent opening should be provided in the liner bag 38 prior to use to prevent the bag from excessive expansion during use. Preferably, the gas vent openings 56 are formed in the bag approximately 0.75 inches, measured along the adjacent tapered edge portion, from the narrowed portion 44. Referring back to FIG. 1, this spaces the gas vent openings 56 from the narrowed portion 44 such that the gas vent openings are not likely to be pressed up against the conventional ostomy bag 12 during use and therefore are likely to be unblocked to permit gas to exit the liner bag 38 and be admitted into an interior 134 of the conventional ostomy bag.

For effective release of gas from the interior 134 of the conventional ostomy bag 12, the conventional ostomy bag should be provided with a vent opening 136, preferably with a conventional carbon filter 138 for removing offensive odours. The relatively small gas vent openings 56 in the liner bag 38 tend to minimize the amount of moisture permitted to escape from the bag and therefore a minimal amount of moisture is provided to the carbon filter 138, which minimizes clogging of the filter. Since clogging of the carbon filter in a conventional ostomy bag is determinative of the time to discard the bag, minimizing clogging of the filter extends the life of the conventional ostomy bag. Since use of the liner bag minimizes clogging of the filter, it also extends the life of the conventional ostomy bag. Typically, one conventional ostomy bag may be used for approximately one week when liners according to the invention are used in conjunction therewith. For a typical ostomy patient, the liner bags are changed each approximately four to six hours and the conventional ostomy bag used in conjunction with the liners is changed approximately once per week, although it will be appreciated that each ostomy patient will have his own schedule and may have to change bag liners and ostomy bags more or less frequently.

Operation

FIG. 5

Figure 5:
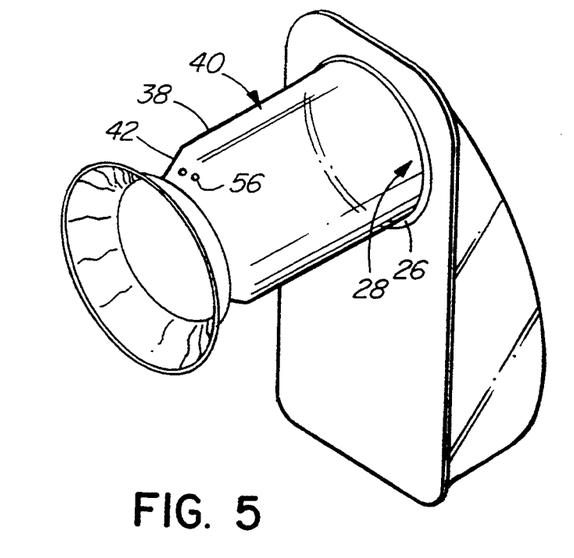
FIG. 5 is a perspective view of a disposable ostomy bag liner according to the first embodiment of the invention, shown being installed in a conventional ostomy bag.

Referring to FIG. 5, the liner bag 38 according to the invention is employed by first inserting the main body portion 40 into the opening 28 in the conventional ostomy bag coupling 26 on a conventional ostomy bag 12. If the liner bag 38 is of the type supplied without gas vent openings 56, the patient should first form the gas vent openings in the tapered portion 42 of the liner prior to inserting the main body portion 40 into the conventional ostomy bag.

FIG. 6

Figure 6:
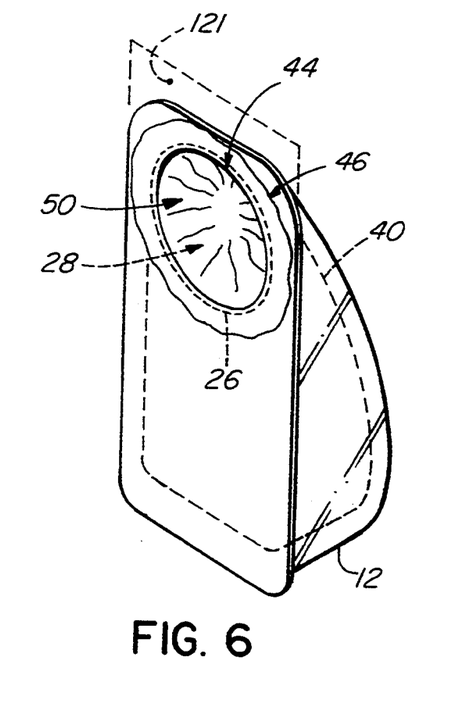
FIG. 6 is a perspective view of the disposable ostomy bag liner shown in FIG. 5, shown installed in a conventional ostomy bag.

Referring to FIG. 6, the main body portion 40 is inserted until the narrowed portion 44 is axially aligned with the bag coupling 26 such that the main body portion is disposed inside the conventional ostomy bag 12 while the flange portion 46 extends outside the conventional ostomy bag. The flange portion 46 is then spread about the bag coupling 26 such that it generally lies flat in a plane parallel to a plane 121 in which the bag coupling lies.

FIG. 7

Figure 7:
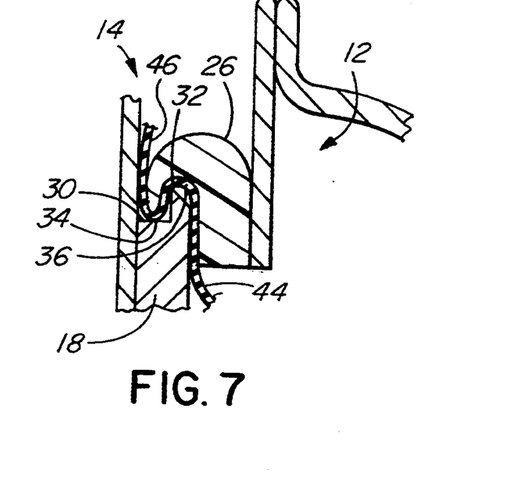
FIG. 7 is a cross sectional view of a flange portion of the disposable ostomy bag liner shown in FIG. 6, shown disposed between the conventional flange coupling and conventional ostomy bag coupling with the conventional flange coupling and conventional ostomy bag coupling joined together, whereby the disposable ostomy bag liner is rendered in sealing engagement with the conventional flange coupling.

Referring to FIG. 7, the bag coupling 26 with the flange portion 46 spread thereabout is pressed onto the flange coupling 18. The flange portion 46 of the liner bag 38 is therefore received between the bag coupling 26 and the flange coupling 18 and more particularly is received between the head portion 32 and groove 36 and between the neck portion 30 and ring 34. Referring back to FIG. 1, the liner is thus secured to the flange coupling 18 in fluid-tight relation such that the mouth opening 50 is operable to receive waste material which would otherwise have been admitted into the conventional ostomy bag 12.

Liquid (and solids) contained in the intestinal waste material is substantially retained in the liner bag 38 and therefore is not permitted to contact the interior portion of the conventional ostomy bag 12. Intestinal gasses are collected in the liner bag 38 but are allowed to escape through the gas vent openings 56 to flow into the interior 134 of the conventional ostomy bag 12 which has the carbon filter 138 and vent opening 136 for permitting these gases to escape to the immediate surroundings. In this way, expansion of the liner bag 38 due to build up of gas pressure is prevented.

The interior 134 of the conventional colostomy bag is kept relatively free of intestinal waste material because the guards, only guard 58 being shown in FIG. 1, act to inhibit access of the waste material to the gas vent openings 56 and the relatively small size of the gas vent openings limits the volume of material which can escape past the guards.

When the liner bag 38 contains a desired amount of intestinal waste, the bag coupling 26 may be removed from the flange coupling 18 by prying the bag coupling therefrom, in a conventional manner already known in the art. It will be appreciated that the transparent nature of the polyethylene sheet forming the bag facilitates a visual check on the quantity of waste material in the liner.

Referring back to FIG. 6, once the bag coupling 26 is removed from the flange coupling 18, the flange portion 46 of the liner bag 38 may then be gathered up, to permit the patient to grasp the liner bag 38, permitting it to be pulled from the conventional ostomy bag 12, through the opening 28. As the flange portion 46 is gathered up, the patient should take care to close the mouth opening 50 by gathering the liner bag 38 at the narrowed portion 44 as this will prevent intestinal waste material from exiting the liner bag 38 through the mouth opening 50. The liner bag with waste material contained therein may then be deposited into a conventional toilet for disposal.

Generally, use of the liner bag involves the basic steps of receiving intestinal waste material in a mouth opening of a disposable ostomy bag liner disposed in an ostomy bag and guarding the waste material, received in the mouth opening, from at least one gas vent opening in the liner to generally inhibit the access of the waste material to the at least one gas vent opening to prevent the waste material from exiting the gas vent opening.

While specific embodiments of the invention have been described and illustrated, such embodiments should be considered illustrative of the invention only and not as limiting the invention as construed in accordance with the accompanying claims.

What is claimed is:

1. A disposable ostomy bag liner apparatus including:
   a) a unitary flexible bag having:
      i) a main body portion defined by first and second joined opposite side edge portions and a bottom joined edge portion extending between the first and second opposite joined edge portions;
      ii) a tapered portion adjacent the main body portion, the tapered portion being defined by first and second tapered joined edges extending from and at respective angles to the first and second joined opposite side edge portions, said main body portion and said tapered portion defining an interior portion of the bag for receiving and holding intestinal waste material;
      iii) a narrowed portion adjacent the tapered portion, for holding the bag in place in an opening of a bag flange on a conventional ostomy bag, said narrowed portion defining a mouth opening in the bag for admitting said intestinal waste material into said interior portion, said tapered portion tapering toward said narrowed portion; and
      iv) a flexible flange portion adjacent the narrowed portion, for cooperating with the ostomy flange to secure and seal the liner to an ostomy flange, the flexible flange portion being at least partially defined by first and second angled, joined flange edges extending from and at respective angles to the first and second tapered joined edges respectively such that said flange portion has an inverse taper and generally extends about said mouth opening; and
      v) a guard disposed in the flexible bag, the guard defining a guarded region in the bag and guarding the waste material received in the mouth opening from said guarded region to generally inhibit the access of the waste material to said guarded region to prevent movement of said waste material into said guarded region.

2. An apparatus as claimed in claim 1 wherein said flexible bag is formed from first and second flexible sheet portions, the first and second flexible sheet portions having joined and unjoined perimeter edge portions, said joined perimeter edge portions generally defining said main body portion, said tapered portion and said narrowed portion, and at least two of said joined perimeter edge portions and said joined perimeter edge portions generally defining said flange portion.

3. An apparatus as claimed in claim 2 wherein said joined edges are laminated together to join corresponding edges on the first and second sheets together.

4. An apparatus as claimed in claim 1 wherein the flange portion extends generally radially beyond the mouth opening by at least approximately 0.5 inches.

5. An apparatus as claimed in claim 1 wherein the angle between the first joined tapered edges and the first joined flange edges is between 60 and 120 degrees.

6. An apparatus as claimed in claim 5 wherein the angle between the first joined tapered edges and the first joined flange edges is approximately 90 degrees.

7. An apparatus as claimed in claim 1 wherein the flexible bag is formed from a disposable material.

8. An apparatus as claimed in claim 7 wherein the disposable material includes a transparent polyethylene plastic having a thickness of between 0.001 and 0.002 inches.

9. A disposable ostomy bag liner apparatus including a unitary flexible bag formed from first and second flexible sheet portions, the first and second flexible sheet portions having joined and unjoined perimeter edge portions, said joined perimeter edge portions generally defining:
   a) a main body portion;
   b) a tapered portion disposed adjacent the main body portion, the main body portion and tapered portion defining an interior portion of the bag for receiving and holding intestinal waste material said tapered portion having a guard disposed therein to define a guarded region in the bag to generally inhibit the access of waste material to said guarded region to prevent movement of said waste material into said guarded region, said guard including a joint line joining the first and second sheet portions together along a line, the guarded portion having at least one gas vent opening disposed therein to vent gas from the interior portion of the bag directly to an interior of a conventional ostomy bag in which the liner may be installed;

c) a narrowed portion disposed adjacent the tapered portion, for holding the bag in place in an opening of a bag flange on said conventional ostomy bag, said narrowed portion defining a mouth opening in the bag for admitting said intestinal waste material into said interior portion; and d) a flexible flange portion adjacent the narrowed portion, defined by at least two of said joined perimeter edge portions, for cooperating with an ostomy flange to secure and seal the liner to said ostomy flange.

10. An apparatus as claimed in claim 9 wherein said at least one gas vent opening includes first and second pairs of gas vent openings.

11. An apparatus as claimed in claim 9 wherein said at least one gas vent opening has a diameter of between approximately 0.02 and 0.03 inches.

12. An apparatus as claimed in claim 9 wherein said joint line extends from a joined perimeter edge portion into the interior portion of the bag.

13. An apparatus as claimed in claim 12 wherein the joint line includes a laminated joint.

14. An apparatus as claimed in claim 9 wherein said flexible bag is formed from a membrane having a thickness of between 0.001 and 0.102 inches, said flange portion having a thickness no greater than the thickness of said membrane, to permit the flange portion to be received between cooperating flanges of a conventional ostomy flange and a conventional ostomy bag.

15. A method of receiving intestinal waste material in a disposable ostomy bag liner, the method comprising the steps of:

a) inserting a main body portion of said ostomy bag liner in an opening in a conventional ostomy bag until a narrowed portion of said liner is axially aligned with a bag coupling on said conventional ostomy bag such that said main body portion is disposed inside said conventional ostomy bag while a flexible flange portion of said liner extends outside the conventional ostomy bag;

b) spreading said flange portion about said bag coupling such that it generally lies flat in a plane parallel to a plane in which the bag coupling lies;

c) pressing the bag coupling with the flange portion spread thereabout, onto the flange coupling such that the flange portion is received between the bag coupling and the flange coupling d) receiving intestinal waste material, in a mouth opening of an ostomy bag liner disposed in an ostomy bag; and e) guarding the waste material, received in said mouth opening, from at least one gas vent opening in said liner to generally inhibit the access of said waste material to said at least one gas vent opening to prevent said waste material from exiting said at least one gas vent opening.

16. A disposable ostomy bag liner comprising:

a) a unitary flexible bag formed from first and second flexible sheet portions respectively, the first and second flexible sheet portions having laminated and unlaminated perimeter edge portions, said laminated perimeter edge portions generally defining;

i) a main body portion;

ii) a tapered portion adjacent the main body portion, the main body portion and tapered portion defining an interior portion of the bag for receiving and hold intestinal waste material;

iii) a narrowed portion adjacent the tapered portion, for holding the bag in place during insertion of the bag in an opening of a bag flange on a conventional ostomy bag, said narrowed portion defining a mouth opening in the bag for admitting said intestinal waste material into said interior portion; and i) a flange portion adjacent the narrowed portion, for cooperating with an ostomy flange to secure and seal the liner to the ostomy flange, the flange portion being defined by at least two of said joined perimeter edge portions and said joined perimeter edge portions b) first and second pairs of gas vent openings disposed generally adjacent respective laminated edge portions generally on opposite sides of said bag; and c) first and second laminated joints joining the first and second flexible sheet portions together along first and second lines respectively, said first and second lines being disposed between said first and second pairs of gas vent openings and said interior portion of said bag respectively and extending from respective laminated edge portions adjacent said first and second pairs of openings respectively, said first and second laminated joints acting to guard the waste material received in the mouth opening from said first and second pairs of gas vent openings respectively to generally inhibit the access of the waste material to said first and second gas vent openings respectively to prevent said waste material from exiting said gas vent openings.

* * * * *